United States Patent
Slazas et al.

(10) Patent No.: US 10,893,963 B2
(45) Date of Patent: Jan. 19, 2021

(54) STENT DELIVERY WITH EXPANSION ASSISTING DELIVERY WIRE

(71) Applicant: DePuy Synthes Products, Inc., Raynham, MA (US)

(72) Inventors: Robert Slazas, Raynham, MA (US); Juan Lorenzo, Raynham, MA (US); Lacey Gorochow, Raynham, MA (US); Pedro Pedroso, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 70 days.

(21) Appl. No.: 16/152,035

(22) Filed: Oct. 4, 2018

(65) Prior Publication Data

US 2020/0038209 A1 Feb. 6, 2020

Related U.S. Application Data

(62) Division of application No. 16/056,065, filed on Aug. 6, 2018, now Pat. No. 10,578,848.

(51) Int. Cl.
*A61F 2/95* (2013.01)
*A61F 2/90* (2013.01)
*A61F 2/82* (2013.01)

(52) U.S. Cl.
CPC .............. *A61F 2/95* (2013.01); *A61F 2/90* (2013.01); *A61F 2002/823* (2013.01);
(Continued)

(58) Field of Classification Search
CPC .. A61F 2/95; A61F 2/962; A61F 2/966; A61F 2002/9505; A61F 2002/9534; A61F 2002/011
See application file for complete search history.

(56) References Cited

U.S. PATENT DOCUMENTS

| 4,332,278 A | 6/1982 | Lalikos |
| 4,610,688 A | 9/1986 | Silvestrini |

(Continued)

FOREIGN PATENT DOCUMENTS

| AL | 0701800 A1 | 3/1996 |
| CN | 101234046 A | 8/2008 |

(Continued)

OTHER PUBLICATIONS

Ansaar T. Rai et al., "Cerebrovascular geometry in the anterior circulation: an analysis of diameter, length and the vessel taper", J NeuroIntervent Surg 2013; 5: 371-375_ doi: 10_ 1136/neurintsurg-2012-010314; Apr. 4, 2012.

(Continued)

*Primary Examiner* — Melanie R Tyson
(74) *Attorney, Agent, or Firm* — Troutman Pepper Hamilton Sanders LLP

(57) ABSTRACT

A method for implanting a stent by providing an implantation system including a catheter, an expandable element, and a delivery wire, moving a first portion of the expandable element to exit the catheter, and maintaining a second portion of the expandable element within the catheter to establish a partially implanted configuration. Then moving the delivery wire independent of the expandable element in the partially implanted configuration, and enlarging a circumference of the expandable element in response to the moving the delivery wire.

4 Claims, 14 Drawing Sheets

(52) U.S. Cl.
CPC ........... *A61F 2002/9505* (2013.01); *A61F 2210/0014* (2013.01); *A61F 2250/0098* (2013.01)

(56) References Cited

U.S. PATENT DOCUMENTS

| | | |
|---|---|---|
| 4,754,685 A | 7/1988 | Kite |
| 5,064,435 A | 11/1991 | Porter |
| 5,282,824 A | 2/1994 | Gianturco |
| 5,330,500 A | 7/1994 | Song |
| 5,382,259 A | 1/1995 | Phelps et al. |
| 5,387,235 A | 2/1995 | Chuter |
| 5,423,849 A | 6/1995 | Engelson |
| 5,476,508 A | 12/1995 | Amstrup |
| 5,522,881 A | 6/1996 | Lentz |
| 5,549,662 A | 8/1996 | Fordenbacher |
| 5,556,413 A | 9/1996 | Lam |
| 5,601,593 A | 2/1997 | Freitag |
| 5,609,627 A | 3/1997 | Goicoechea |
| 5,645,558 A | 7/1997 | Horton |
| 5,662,622 A | 9/1997 | Gore |
| 5,702,418 A | 12/1997 | Ravenscroft |
| 5,725,549 A | 3/1998 | Lam |
| 5,728,131 A | 3/1998 | Frantzen |
| 5,755,772 A | 5/1998 | Evans et al. |
| 5,769,887 A | 6/1998 | Brown |
| 5,776,161 A | 7/1998 | Globerman |
| 5,817,126 A | 10/1998 | Imran |
| 5,849,037 A | 12/1998 | Frid |
| 5,851,217 A | 12/1998 | Wolff |
| 5,899,935 A | 5/1999 | Ding |
| 5,916,235 A | 6/1999 | Guglielmi |
| 5,916,264 A | 6/1999 | Von Oepen |
| 5,961,546 A | 10/1999 | Robinson et al. |
| 6,010,529 A | 1/2000 | Herweck |
| 6,015,432 A | 1/2000 | Rakos et al. |
| 6,033,436 A | 3/2000 | Steinke |
| 6,036,725 A | 3/2000 | Avellanet |
| 6,051,020 A | 4/2000 | Goicoechea |
| 6,099,559 A | 8/2000 | Nolting |
| 6,110,198 A | 8/2000 | Fogarty |
| 6,123,722 A | 9/2000 | Fogarty et al. |
| 6,123,723 A | 9/2000 | Konya et al. |
| 6,152,956 A | 11/2000 | Pierce |
| 6,161,399 A | 12/2000 | Jayaraman |
| 6,165,213 A | 12/2000 | Goicoechea |
| 6,168,621 B1 | 1/2001 | Vrba |
| 6,176,875 B1 | 1/2001 | Lenker |
| 6,264,683 B1 | 7/2001 | Stack et al. |
| 6,280,465 B1 | 8/2001 | Cryer |
| 6,319,278 B1 | 11/2001 | Quinn |
| 6,325,823 B1 | 12/2001 | Horzewski |
| 6,348,066 B1 | 2/2002 | Pinchuk et al. |
| 6,409,755 B1 | 6/2002 | Vrba |
| 6,488,702 B1 | 12/2002 | Besselink |
| 6,612,012 B2 | 9/2003 | Mitelberg et al. |
| 6,626,936 B2 | 9/2003 | Stinson |
| 6,635,080 B1 | 10/2003 | Lauterjung et al. |
| 6,673,106 B2 | 1/2004 | Mitelberg |
| 6,699,277 B1 | 3/2004 | Freidberg et al. |
| 6,740,113 B2 | 5/2004 | Vrba |
| 6,673,107 B1 | 6/2004 | Brandt |
| 6,770,089 B1 | 8/2004 | Hong et al. |
| 6,818,013 B2 | 11/2004 | Mitelberg |
| 6,833,003 B2 | 12/2004 | Jones |
| 6,899,914 B2 | 5/2005 | Schmitz |
| 6,911,040 B2 | 6/2005 | Johnson et al. |
| 6,918,928 B2 | 7/2005 | Wolinsky |
| 6,929,659 B2 | 8/2005 | Pinchuk |
| 6,945,994 B2 | 9/2005 | Austin et al. |
| 6,955,685 B2 | 10/2005 | Escamilla |
| 6,960,227 B2 | 11/2005 | Jones |
| 6,960,228 B2 | 11/2005 | Mitelberg et al. |
| 6,970,734 B2 | 11/2005 | Eidenschink |
| 7,001,422 B2 | 2/2006 | Escamilla |
| 7,037,331 B2 | 5/2006 | Mitelberg |
| 7,122,052 B2 | 10/2006 | Greenhaigh |
| 7,201,769 B2 | 4/2007 | Jones et al. |
| 7,208,008 B2 | 4/2007 | Clarke |
| 7,267,685 B2 | 9/2007 | Butaric |
| 7,288,111 B1 | 10/2007 | Holloway et al. |
| 7,291,167 B2 | 11/2007 | DiCaprio |
| 7,309,351 B2 | 12/2007 | Escamilla et al. |
| 7,344,559 B2 | 3/2008 | Gray |
| 7,462,190 B2 | 12/2008 | Lombardi |
| 7,480,973 B2 | 1/2009 | Miller |
| 7,628,806 B2 | 12/2009 | Yampolsky et al. |
| 7,632,302 B2 | 12/2009 | Vreeman et al. |
| 7,641,647 B2 | 1/2010 | Gunderson |
| 7,655,031 B2 | 2/2010 | Tenne et al. |
| 7,655,034 B2 | 2/2010 | Mitchell et al. |
| 7,708,773 B2 | 5/2010 | Pinchuk et al. |
| 7,758,629 B2 | 7/2010 | Holloway et al. |
| 7,761,138 B2 | 7/2010 | Wang |
| 7,806,919 B2 | 10/2010 | Bloom et al. |
| 7,806,923 B2 | 10/2010 | Moloney |
| RE42,244 E | 3/2011 | Boatman |
| 7,913,371 B2 | 3/2011 | Klocke |
| 7,985,213 B2 | 7/2011 | Parker |
| 7,998,187 B2 | 8/2011 | Hartley et al. |
| 8,021,418 B2 | 9/2011 | Gerberding |
| 8,043,353 B2 | 10/2011 | Kaufmann et al. |
| 8,043,357 B2 | 10/2011 | Hartley |
| 8,048,139 B2 | 11/2011 | Frid et al. |
| 8,092,510 B2 | 1/2012 | Metcalf et al. |
| 8,142,456 B2 | 3/2012 | Rosqueta |
| 8,152,833 B2 | 4/2012 | Zaver |
| 8,182,523 B2 | 5/2012 | Tenne et al. |
| 8,187,316 B2 | 5/2012 | Kuppurathanam |
| 8,357,194 B2 | 1/2013 | Majercak |
| 8,372,133 B2 | 2/2013 | Douk et al. |
| 8,394,119 B2 | 3/2013 | Zaver |
| 8,449,600 B2 | 5/2013 | Hartley et al. |
| 8,562,666 B2 | 10/2013 | Bonsignore |
| 8,579,959 B2 | 11/2013 | Ducke |
| 8,597,276 B2 | 12/2013 | Vongphakdy et al. |
| 8,641,748 B2 | 2/2014 | Hebert et al. |
| 8,672,992 B2 | 3/2014 | Orr |
| 8,709,065 B2 | 4/2014 | Chobotov |
| 8,734,501 B2 | 5/2014 | Hartley et al. |
| 8,778,008 B2 | 7/2014 | Amplatz et al. |
| 8,816,247 B1 | 8/2014 | Janardhan et al. |
| 8,864,811 B2 | 10/2014 | Kao |
| 9,078,731 B2 | 7/2015 | Mortarino |
| 9,301,864 B2 | 4/2016 | Kao |
| 9,320,590 B2 | 4/2016 | Zaver |
| 9,339,260 B2 | 5/2016 | Eidenschink et al. |
| 9,427,343 B2 | 8/2016 | Bogert |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |

(56) References Cited

U.S. PATENT DOCUMENTS

| | | |
|---|---|---|
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 10,076,428 B2 | 9/2018 | Gorochow |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0188344 A1 | 12/2002 | Bolea |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0236406 A1 | 11/2004 | Gregorich |
| 2004/0254637 A1 | 12/2004 | Yang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0148866 A1 | 7/2005 | Gunderson |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0069424 A1 | 3/2006 | Acosta |
| 2006/0195175 A1 | 8/2006 | Bregulla |
| 2006/0212113 A1 | 9/2006 | Shaolian et al. |
| 2006/0271153 A1* | 11/2006 | Garcia ............ A61B 17/12022 623/1.11 |
| 2006/0287717 A1 | 12/2006 | Rowe |
| 2007/0005127 A1 | 1/2007 | Boekstegers |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0213810 A1 | 9/2007 | Newhauser |
| 2007/0219612 A1 | 9/2007 | Andreas |
| 2007/0219613 A1 | 9/2007 | Kao |
| 2007/0233223 A1 | 10/2007 | Styrc |
| 2007/0233224 A1 | 10/2007 | Leynov |
| 2007/0238979 A1 | 10/2007 | Huynh |
| 2007/0255385 A1 | 11/2007 | Tenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0192588 A1 | 7/2009 | Shin |
| 2009/0198315 A1 | 8/2009 | Boudjemline |
| 2009/0248133 A1 | 10/2009 | Bloom |
| 2009/0287145 A1 | 11/2009 | Cragg |
| 2009/0326640 A1 | 12/2009 | Yoshimura |
| 2010/0010619 A1 | 1/2010 | Tischler |
| 2010/0010622 A1 | 1/2010 | Lowe |
| 2010/0069948 A1 | 3/2010 | Veznedaroglu |
| 2010/0161028 A1 | 6/2010 | Chuter |
| 2010/0161036 A1 | 6/2010 | Pintor |
| 2010/0234935 A1 | 9/2010 | Bashiri |
| 2010/0274282 A1 | 10/2010 | Olson |
| 2013/0245745 A1 | 9/2013 | Vong et al. |
| 2014/0200648 A1 | 7/2014 | Newell et al. |
| 2014/0277332 A1 | 9/2014 | Slazas et al. |
| 2015/0025625 A1 | 1/2015 | Rylski et al. |
| 2015/0148882 A1 | 5/2015 | Ma et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |

(56) References Cited

U.S. PATENT DOCUMENTS

| | | |
|---|---|---|
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0196689 A1 | 7/2017 | Salahieh |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265870 A1 | 9/2017 | Kealey et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281375 A1 | 10/2017 | Longo |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290653 A1 | 10/2017 | Folan et al. |
| 2017/0290654 A1 | 10/2017 | Sethna |
| 2017/0290686 A1 | 10/2017 | Sirhan |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0092766 A1 | 4/2018 | Gorochow |
| 2018/0263794 A1 | 9/2018 | Slazas et al. |
| 2019/0015229 A1 | 1/2019 | Fukutaki |
| 2019/0053899 A1 | 2/2019 | Levi |
| 2019/0224008 A1 | 7/2019 | Bressloff |

FOREIGN PATENT DOCUMENTS

| | | |
|---|---|---|
| CN | 102271620 A | 12/2011 |
| CN | 103347466 A | 10/2013 |
| DE | 202008014828 U1 | 2/2009 |
| DE | 102011015995 A1 | 10/2012 |
| DE | 10 2014 113836 A1 | 3/2016 |
| EP | 0894505 A2 | 2/1999 |
| EP | 1488763 A2 | 12/2004 |
| EP | 1634546 A1 | 3/2006 |
| EP | 2545887 A1 | 1/2013 |
| EP | 2 777 642 A1 | 9/2014 |
| EP | 2777638 A1 | 9/2014 |
| EP | 2777649 A1 | 9/2014 |
| EP | 2915509 A1 | 9/2015 |
| EP | 3 311 782 A1 | 4/2018 |
| FR | 2939637 A1 | 6/2010 |
| JP | 3-503246 A | 7/1991 |
| JP | 11-57010 A | 3/1999 |
| JP | 11-57020 A | 3/1999 |
| JP | 2004-267750 A | 9/2004 |
| WO | 1989/008433 A1 | 9/1989 |
| WO | 99/43379 A1 | 9/1999 |
| WO | 2001/015632 A1 | 3/2001 |
| WO | 01/35864 A1 | 5/2001 |
| WO | 2001/058384 A1 | 8/2001 |
| WO | 2001/072240 A1 | 10/2001 |
| WO | 2005/087138 A1 | 9/2005 |
| WO | 2008/130530 A1 | 10/2008 |
| WO | 2018/082440 A1 | 6/2012 |
| WO | 2012/096687 A1 | 7/2012 |
| WO | 2013/126299 A1 | 8/2013 |
| WO | 2013/151793 A1 | 10/2013 |

OTHER PUBLICATIONS

MIG-WELDING.CO.UK; Excerpt from with comment of Jun. 29, 2011 on pictures of welds. remove 141.

Mitcale.com; Welded connections excerpt, downloaded Dec. 6, 2012 remove 141.

Navigate Tough Anatomy; brochure Copyright 2009; Codman & Shurtleff, Inc., 325 Paramount Drive, Raynham, Massachusetts remove 141.

Plug Weld Joining Two Plates; Excerpt from esabna.com, downloaded Dec. 6, 2012 remove 141.

Extended European Search Report issued in corresponding European Patent Application No. 19190059.6 dated Jan. 8, 2020.

Extended European Search Report issued in corresponding European Patent Application No. 19 21 9438 dated Apr. 7, 2020.

* cited by examiner

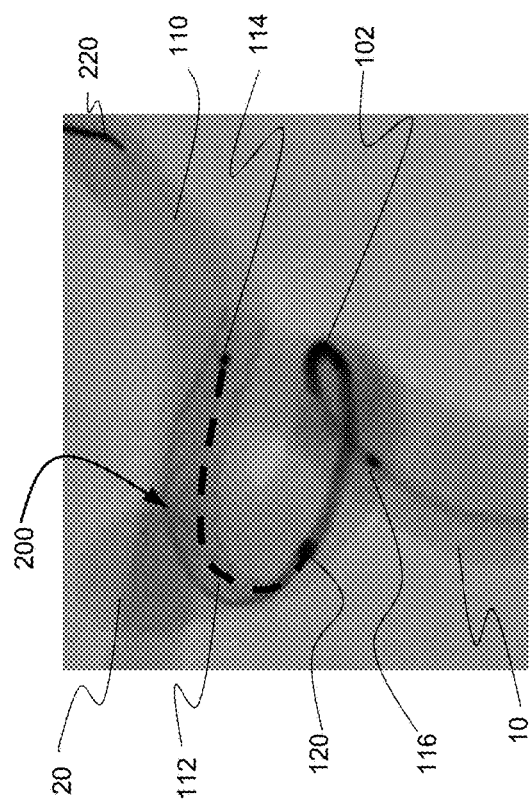
FIG. 6A
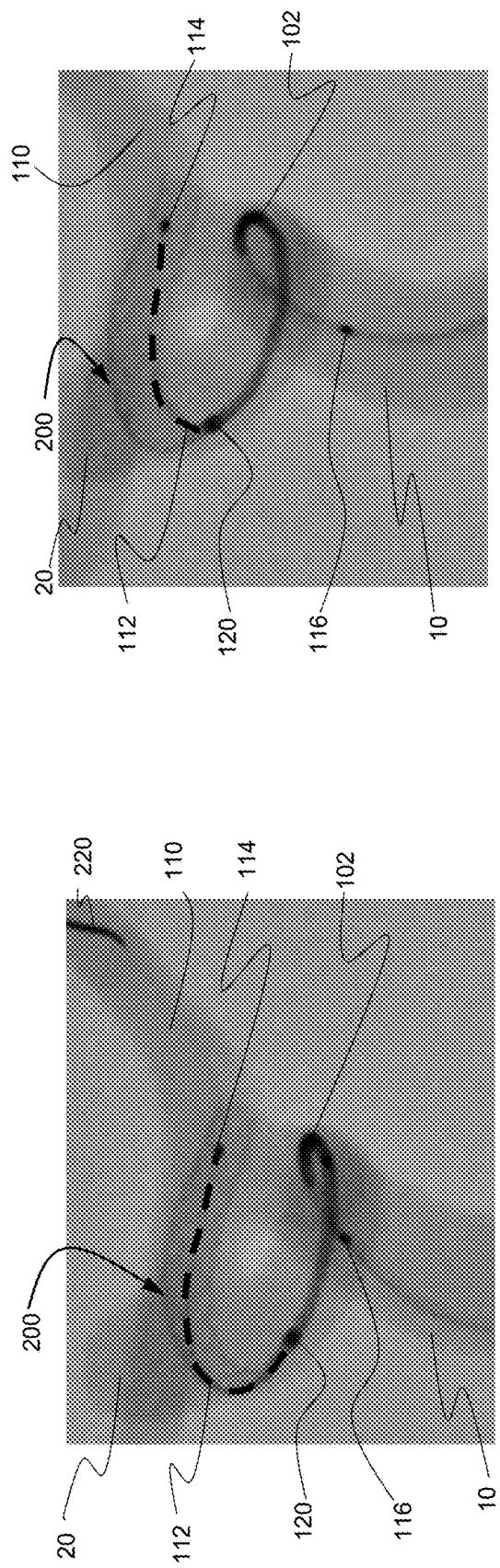
FIG. 6B
FIG. 6C

STENT DELIVERY WITH EXPANSION ASSISTING DELIVERY WIRE

CROSS-REFERENCE TO RELATED APPLICATIONS

This application is a divisional of U.S. application Ser. No. 16/056,065 filed on Aug. 6, 2018, the content of which is incorporated herein by reference in its entirety.

FIELD OF INVENTION

The present invention generally relates to methods for interventional therapeutic treatment or vascular surgery for treatment of defects in the vasculature, and more particularly to delivering a stent to a treatment site in a body lumen of a patient and opening the stent at the treatment site.

BACKGROUND

Stents are inserted into a blood vessel to provide an open path within the blood vessel, and they have been widely used intravascular angioplasty treatment of occluded blood vessels and other applications. Stents can be self-expanding or can be expanded by a radial force applied from inside the stent, for example when the stent is fitted with a balloon.

A braided stent can be characterized by a tube of metal wires woven together with a plain weaving technique. During delivery to a treatment site, a braided stent can travel through a catheter in an elongated, collapsed configuration, having a small diameter, and the braided stent can enlarge in diameter at a treatment site. Proper treatment with a braided stent can require that the stent extend radially to the walls of the body lumen in which the stent is implanted. Although braided stents can be self-expanding, such implants typically open with low opening forces, and therefore may not fully open to conform to a vessel wall. Post deployment, ancillary devices such as guidewires, catheters, balloons, etc. can be used to cross the braid and attempt to further expand the braided stent to improve vessel wall conformity. Issues such as unintentional braid movement or inability to fully open the braid commonly occur. Further, a braided implant that is separated from a delivery wire cannot be recovered for repositioning.

SUMMARY

It is an object of the present invention to provide systems, devices, and methods for improving vessel wall conformity of a braided stent. Generally, an expandable element having a distal anchor member at a distal end, a proximal anchor member at a proximal end, and a braided intermediate portion can be delivered to a treatment site through a catheter by a delivery wire having a first, distal bump that can be translated distally to push the distal anchor distally and release the distal anchor upon exiting a distal end of the catheter, a shaped segment that can be moved to apply a radial force from within the braided intermediate portion to expand the braided intermediate portion, and a second, proximal bump that can be translated distally to push the proximal anchor distally and expel the expandable element from the catheter.

The delivery wire can also have a third, recapture bump positioned proximal the distal bump and distal the proximal bump that can be translated proximally to push the proximal anchor proximally. A partially implanted expandable element having a distal portion expelled from the catheter and released from the delivery wire and a proximal anchor positioned within the catheter can be retracted by translating the delivery wire proximally to push the proximal anchor proximally, thereby pulling the braided portion and distal anchor proximally into the catheter.

An example vascular treatment apparatus can include a catheter, an expandable element, and a delivery wire. The catheter can have an inner lumen through which the expandable element can be delivered by the delivery wire to a treatment site. The expandable element can have a proximal end, a distal end, a braided portion located between the proximal end and the distal end, a proximal anchor member disposed at the proximal end, and a distal anchor member disposed at the distal end.

The expandable element can have a compressed configuration dimensioned to fit within the inner lumen of the catheter for delivery to the treatment site and a partially implanted configuration when the expandable element is not fully implanted at the treatment site. In the partially implanted configuration, the proximal end of the expandable element can be dimensioned to fit within the inner lumen of the catheter, and the distal end can be dimensioned larger than the catheter.

The delivery wire can be disposed within and extend through the inner lumen of the catheter and the expandable element, the expandable element having a substantially tubular shape. The delivery wire can have a proximal portion, a proximal bump member located at a distal end of the proximal portion, a distal portion, a distal bump member located at a proximal end of the distal portion, and a shapeable portion located between the proximal bump member and the distal bump. The shapeable portion can be movable from a substantially straight configuration to a curved configuration upon exiting the inner lumen of the catheter.

The expandable element can be movable from the compressed configuration to the partially implanted configuration by a distal movement of the delivery wire which can cause the distal bump member of the delivery wire to engage with the distal anchor member of the expandable element and push the distal anchor member distally. The distal anchor member can be expelled from the catheter pushing the distal anchor member out of the catheter with the distal bump member.

The delivery wire can be moved distally, proximally, and rotationally in relation to the expandable element in the partially implanted configuration, and the shapeable portion of the delivery wire can be moved to provide a radial force from within the braided portion of the expandable element when the expandable element is in the partially implanted configuration.

The shapeable portion can be movable to at least one of a symmetrical arc shape, an asymmetrical arc shape, or an approximate "S" shape in the curved configuration.

The expandable element can be in the compressed configuration and positioned entirely within the inner lumen of the catheter. When the expandable element is in the compressed configuration and positioned entirely within the inner lumen of the catheter, the shaped portion can be in the substantially straight configuration and can be positioned within a lumen of the braided portion of the expandable element, the distal bump member can be positioned within the lumen of the braided portion of the expandable element, and the proximal bump member can be positioned proximal the proximal anchor member.

The expandable element can be in the partially implanted configuration such that the distal end of the expandable element is positioned outside the catheter and the proximal end and the proximal anchor of the expandable element are positioned within the inner lumen of the catheter. When the expandable element is in the partially implanted configuration, the shapeable portion of the delivery wire can be in the curved configuration and positioned outside the catheter, and a rotation of the delivery wire in relation to the expandable element can expand a radius of the expandable element.

An example method for implanting a stent can include the steps of: providing an implantation system comprising a catheter, an expandable element, and a delivery wire; moving a first portion of the expandable element to exit the catheter; maintaining a second portion of the expandable element within the catheter to establish a partially implanted configuration; moving the delivery wire independent of the expandable element in the partially implanted configuration; and enlarging a circumference of the expandable element in response to the moving the delivery wire. The method can further include the steps of positioning a proximal anchor at a proximal end of the expandable element; positioning a distal anchor at a distal end of the expandable element; positioning a distal bump on the delivery wire; positioning a proximal bump on the delivery wire proximal to the distal bump; positioning the distal bump within a lumen of the expandable element; positioning the proximal bump proximal to the expandable element; positioning the expandable element and at least a portion of the delivery wire within a lumen of the catheter; and moving the distal anchor and the expandable element distally through the lumen of the catheter by pushing the delivery wire distally thereby pushing the distal bump against the distal anchor; expelling the proximal anchor from the distal end of the catheter by pushing the delivery wire distally thereby pushing the proximal bump against the proximal anchor; and expanding the expelled proximal anchor.

The step of moving a first portion of the expandable element to exit the catheter can include the steps of expelling the distal anchor from a distal end of the catheter by pushing the delivery wire distally thereby pushing the distal bump against the distal anchor; and expanding the expelled distal anchor.

The step of moving the delivery wire independent of the expandable element in the partially implanted configuration can include the step of maintaining the proximal anchor within the lumen of the catheter.

The step of enlarging a circumference of the expandable element in response to the moving the delivery wire can include the step of providing a radial force from the delivery wire against the expandable element from within the lumen of the expandable element.

The method can further include the steps of shaping a portion of the delivery wire from a substantially straight configuration to a curved configuration upon a distal movement of the portion from within the lumen of the catheter to a position outside the lumen of the catheter; sliding the shaped portion of the delivery wire against the expandable element from within the lumen of the expandable element; extending a portion of the expandable element to a wall of a vascular by moving the shaped portion against the expandable element; and moving the second portion of the expandable element to exit the catheter and become implanted by pushing the expandable element distally with a distal movement of the delivery wire.

An example system for implanting a stent or other such expandable element can include a catheter, a braided stent, and a delivery wire. The braided stent can be movable to a partially implanted configuration characterized by a portion of the braided stent exterior to the catheter and a portion of the braided stent within the catheter, and the delivery wire can be movable independent of the braided stent and movable to provide a force to open the braided stent when the braided stent is in a partially implanted configuration.

The braided stent can be moved in a compressed configuration through the catheter and can be movable from the compressed configuration to the partially implanted configuration. The braided stent of the system can have a first expandable anchor at a distal end and a second expandable anchor at a proximal end, such that, in the partially implanted configuration, the first expandable anchor is expanded in an implanted position distal to the catheter and the second expandable anchor is compressed within the catheter.

The delivery wire can be movable in a distal direction, a proximal direction, and in a rotational direction independent of the braided stent when the braided stent is in the partially implanted configuration. The delivery wire can extend through the braided stent when the braided stent is in the compressed configuration and when the braided stent is in the partially implanted configuration.

The delivery wire can include a pusher bump that can be positioned proximal the second expandable anchor when the braided stent is in the compressed configuration and when the braided stent is in the partially implanted configuration. The pusher bump can be movable to push the second expandable anchor distally thereby pushing the braided stent distally when the braided stent is in the partially implanted configuration.

The delivery wire can include a shapeable segment that can be positioned within the braided stent when the braided stent is in the compressed configuration and when the braided stent is in the partially implanted configuration. The shapeable segment can be movable from a substantially straight configuration when the braided stent is in the compressed configuration to a curved configuration when the braided stent is in the partially implanted configuration, and the shapeable segment can be movable independent of the braided stent when the braided stent is in the partially implanted configuration. The shapeable segment can be movable to form an arc shape, an undulating shape, or other atraumatic shape when in the curved configuration.

The delivery wire can include a puller bump positioned distal the pusher bump and the shapeable segment and also positioned proximal the first expandable anchor when the braided stent is in the compressed configuration.

BRIEF DESCRIPTION OF THE DRAWINGS

The above and further aspects of this invention are further discussed with reference to the following description in conjunction with the accompanying Figures, in which like numerals indicate like structural elements and features in various Figures. Images and drawings in the Figures are not necessarily to scale, emphasis instead being placed upon illustrating principles of the invention. As indicated, the Figures depict one or more implementations of the inventive devices, by way of example only, not by way of limitation.

FIGS. 6A to 6C are images illustrating steps for use of an implantation system according to the present invention.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
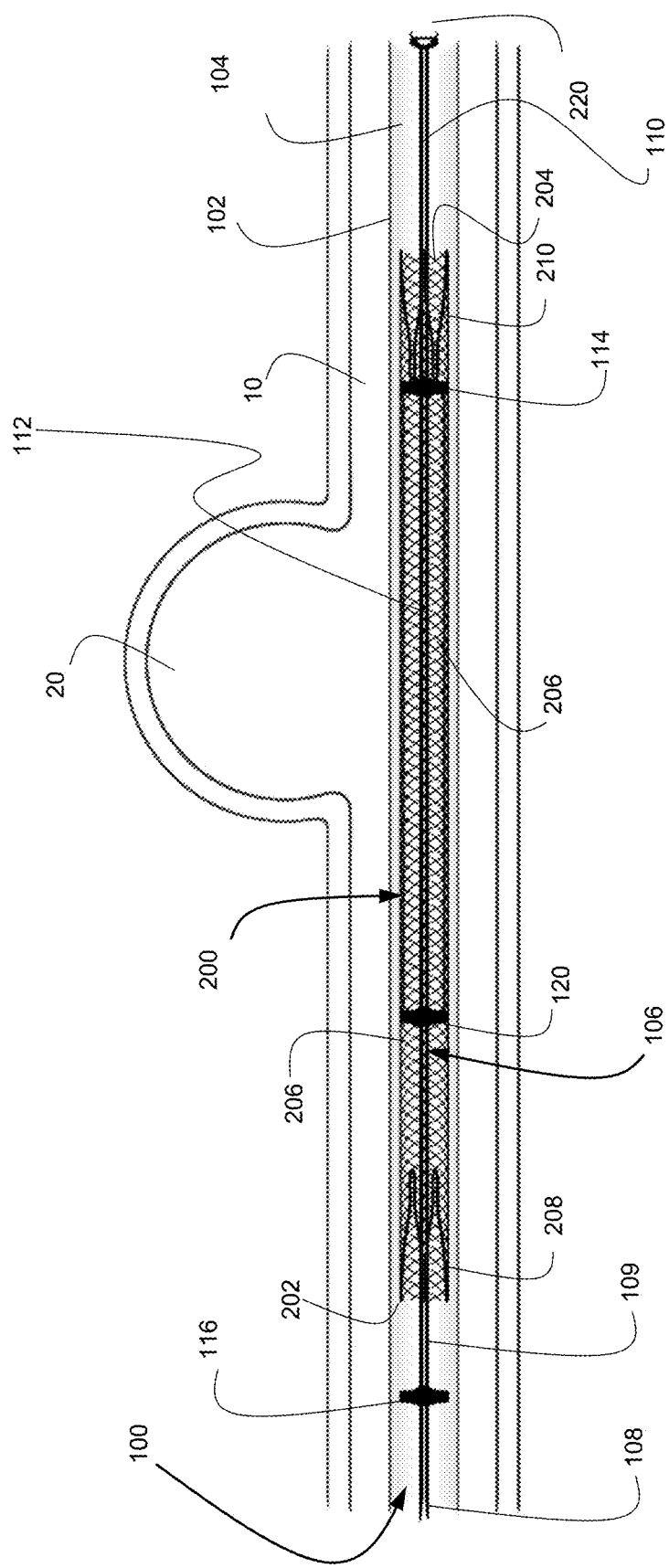
FIG. 1 is a drawing depicting an implantation system in a delivery configuration according to the present invention.

An example of an implantation system 100, as illustrated in FIG. 1 can have a catheter 102, an expandable element 200, and a delivery wire 106. The catheter 102 can have an inner lumen 104, and the expandable element 200 can be formed into a compressed configuration that is dimensioned to fit within the inner lumen 104 of the catheter 102. The expandable element 200 can have a proximal end 202, a distal end 204, a braided portion 206 located between the proximal end 202 and the distal end 204, a proximal anchor member 208 disposed at the proximal end 202, and a distal anchor member 210 disposed at the distal end 204. The delivery wire 106 can be disposed within and extend through the inner lumen 104 of the catheter 102 and the expandable element 200 and can be used to deliver the expandable element 200 to a treatment site and position the expandable element 200 at the treatment site. The delivery wire 106 can have a proximal portion 108, a distal portion 110, a proximal bump member 114 located at a distal end of the proximal portion 108, a distal bump member 114 located at a proximal end of the distal portion 110, and a shapeable portion 112 located between the proximal bump member 116 and the distal bump member 114. When the expandable element 200 is in the compressed configuration for delivery through the catheter 102, the shapeable portion 112 can have a substantially straight shape that has flexibility to navigate through a catheter 102 to a treatment site.

The delivery wire 106 can further include a recapture bump 120 positioned between the distal bump 114 and the proximal bump 116. In such a configuration, the delivery wire 106 can include a segment 109 between the recapture bump 120 and the proximal bump 116. Delivery, positioning, retraction of an expandable element such as a stent within a body lumen utilizing a delivery wire having a distal bump member, proximal bump member, and a recapture bump is the subject of another patent application filed concurrently with this application.

One or all of the bump members 114, 116, 120 can include a radiopaque material to allow the location of the bumps 144, 116, 120 to be readily visible during an implanting procedure.

The one or more anchor members 208, 210, can be projections which extend generally parallel to a longitudinal axis of the expandable element 200 and extend downward toward the longitudinal axis of the expandable element 200. The anchor members 208, 210 can serve as a radiopaque marker for improved visualization during the deployment of the expandable element 200 within the body lumen 10. The anchor members 208, 210 can be used to align the expandable element 200 so it can be pushed and pulled through the catheter 102 without damage or deformation. The anchor members 208, 210 can also be used to move the braided portion 206 into an expanded/implanted configuration. An example of the anchor member 208, 210 can be found in U.S. Ser. No. 15/299,918, the entirety of which is incorporated herein by reference.

Typically, the expandable element 200 can have a compressed configuration and an expanded, implanted, configuration. In the compressed configuration the expandable element 200 can be dimensioned to fit within the inner lumen 104 of the catheter 102. In certain examples, the catheter 102 can aid in constraining the expandable element 200 so it does not expand when contained within the catheter 102. Other elements can be used to constrain the expandable element 200 as are known in the art.

The expandable element 200 can also have a partially implanted configuration where the proximal end 202 is dimensioned to fit within the inner lumen 104 of the catheter 102 and the distal end 204 is dimensioned larger than the catheter 102.

Figure 2A:
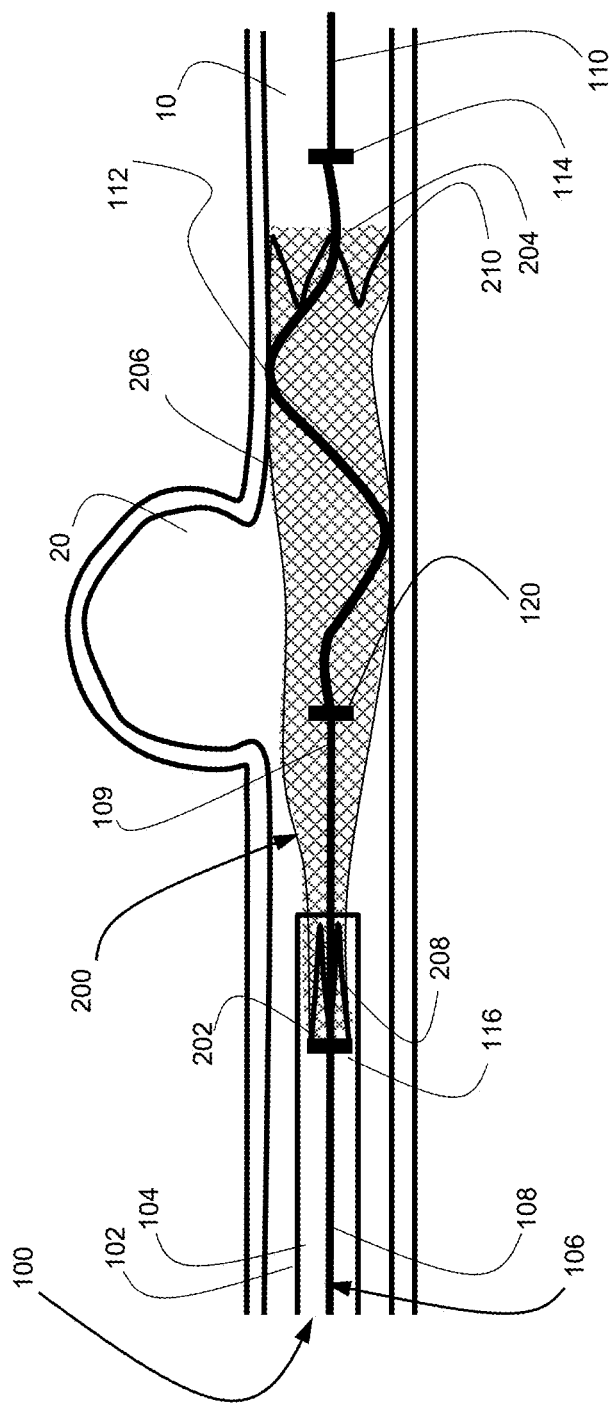
FIGS. 2A to 2H are drawings illustrating steps for use of an implantation system according to the present invention.

FIGS. 2A to 2H are drawings illustrating steps for use of an implantation system. When the expandable element 200 is in the collapsed configuration, the distal bump 114 can be positioned inside the expandable element 200 such that a distal movement of the delivery wire 106 can cause the distal bump 114 to push against the distal anchor 210, pulling the expandable anchor 200 through the catheter 102 to a treatment site. The distal bump member 114 can push the distal anchor member 210 to expel the distal anchor member 210 from the catheter 102, thereby moving the expandable element 200 to a partially implanted configuration as illustrated in FIG. 2A.

Upon exiting the catheter, the shapeable portion 112 of the delivery wire 106 can move from a straight shape to a curved shape as illustrated in FIGS. 2A to 2H. The shapeable portion 112 can provide a radial force from within the braided portion 206 of the expandable element 200 when the expandable element is in the partially implanted configuration.

In an example, the entire delivery wire 106, including the shapeable portion 112, can be made of stainless steel. In other examples, the delivery wire 106 and/or the shapeable portion 112 can be made of a memory shape material including a memory shape metal such as Nitinol or a polymeric memory shape material. The shapeable portion 112 can move from a substantially straight flexible configuration while in the catheter 102 to a curved configuration upon contacting bodily fluid when exiting the catheter 102. Additionally or alternatively, the shapeable portion 112 can curve to conform to the shape of a curved bodily lumen such that distal and proximal movements of the expandable element 200, delivery wire 106, and catheter 102 can cause the delivery wire 106 to move to provide a radial force from within the braided portion 206.

As illustrated in FIG. 2A, during treatment, because self-expanding braided implants may provide a low radial force during implantation, at least some of the intermediate portion 206 of the expandable element 200 may not fully conform to the walls of a body lumen 10.

Figure 2B:
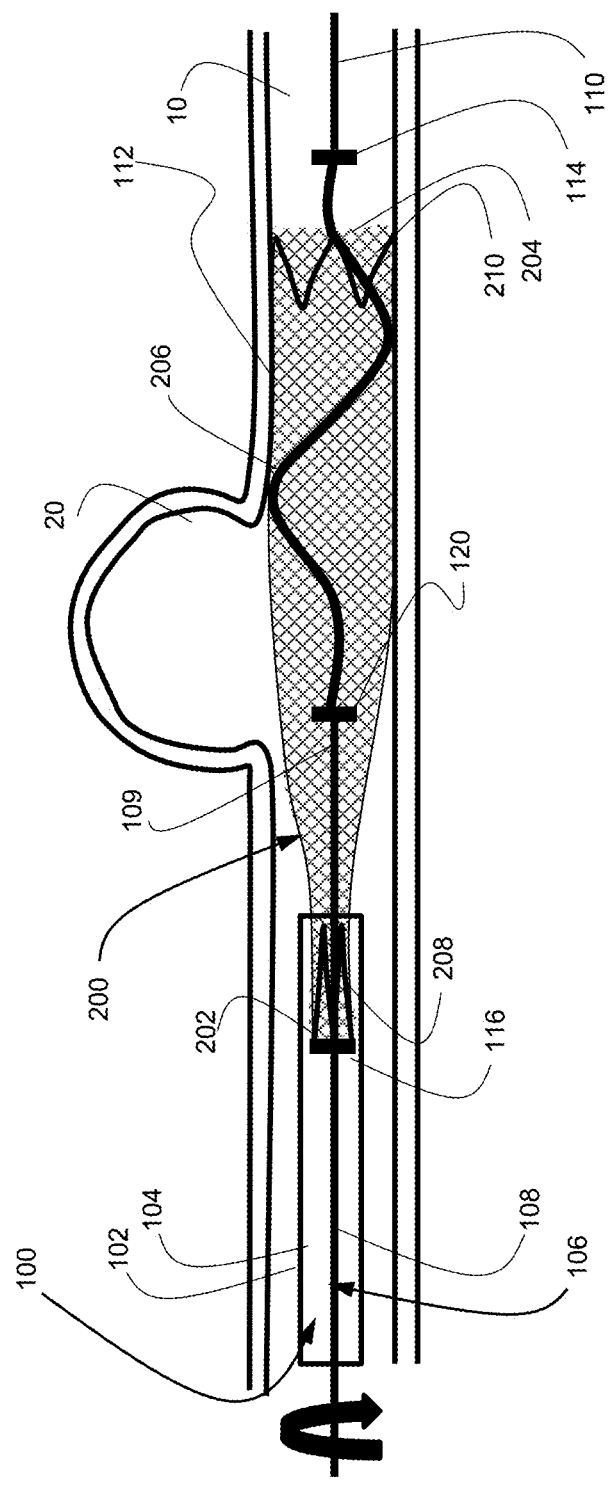

As illustrated in FIG. 2B, the delivery wire 106 can be rotatable in relation to the expandable element 200, and the rotation can cause the shaped portion 112 of the delivery wire 106 to provide a force against the expandable element 200, pushing portions of the expandable element to conform to the walls of the body lumen 10.

Figure 2C:
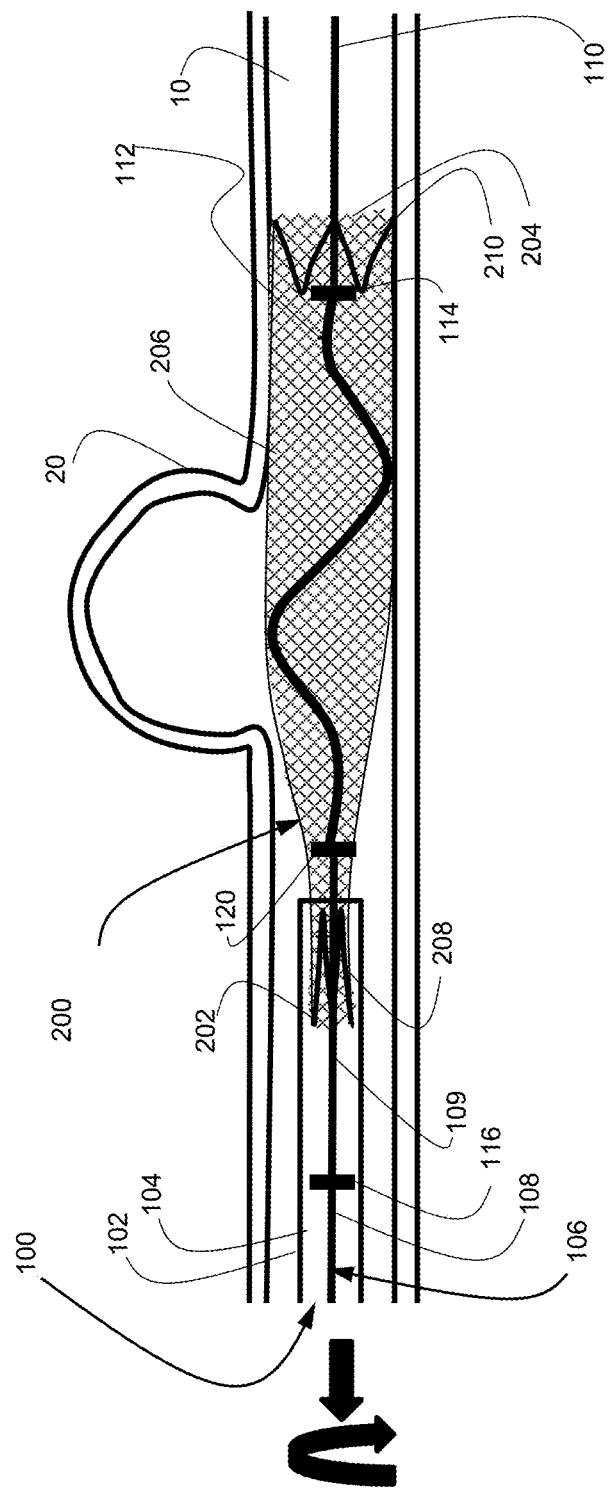

As illustrated in FIG. 2C, the delivery wire 106 can be movable in a distal and a proximal direction in relation to the expandable element 200 without disturbing the placement of the partially implanted expandable element 200. The distal and proximal movement can also cause the shaped portion 112 of the delivery wire 106 to move against the expandable element 200, causing portions of the expandable element 200 to better conform to the walls of the body lumen 10.

Figure 2D:
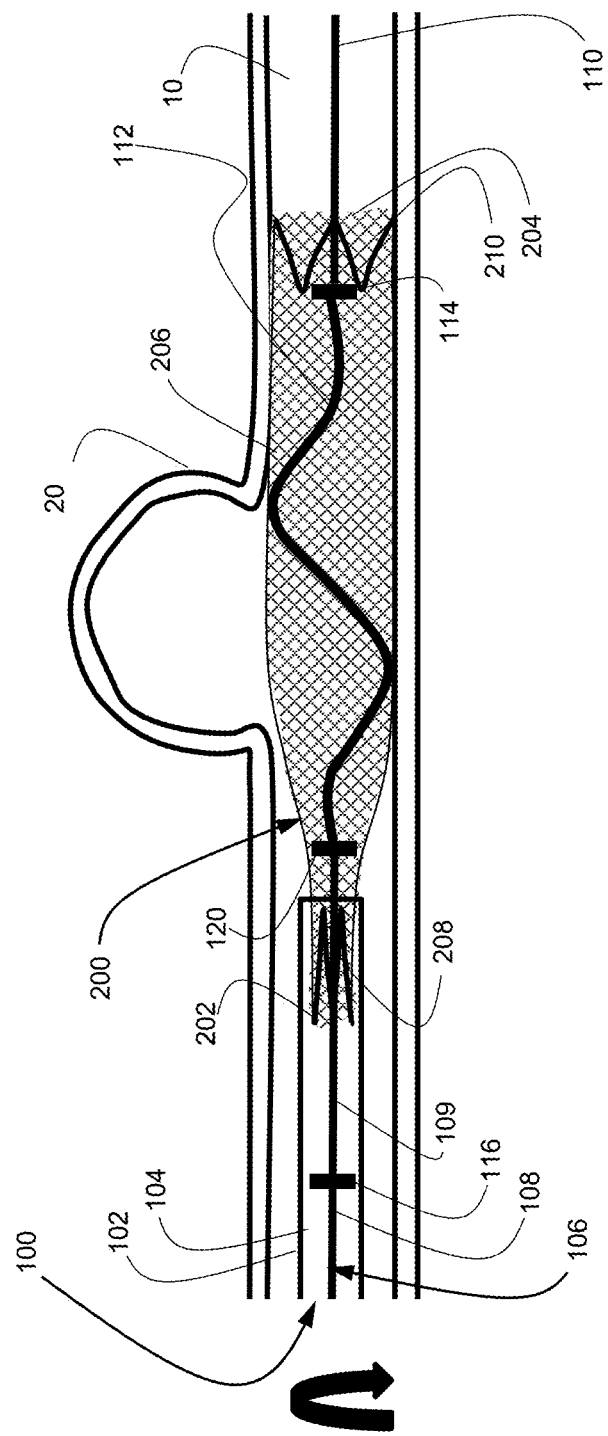

As illustrated in FIG. 2D, the delivery wire 106 can be subsequently rotated to improve conformity of the expandable element 200 to the walls of the body lumen 10.

Figure 2E:
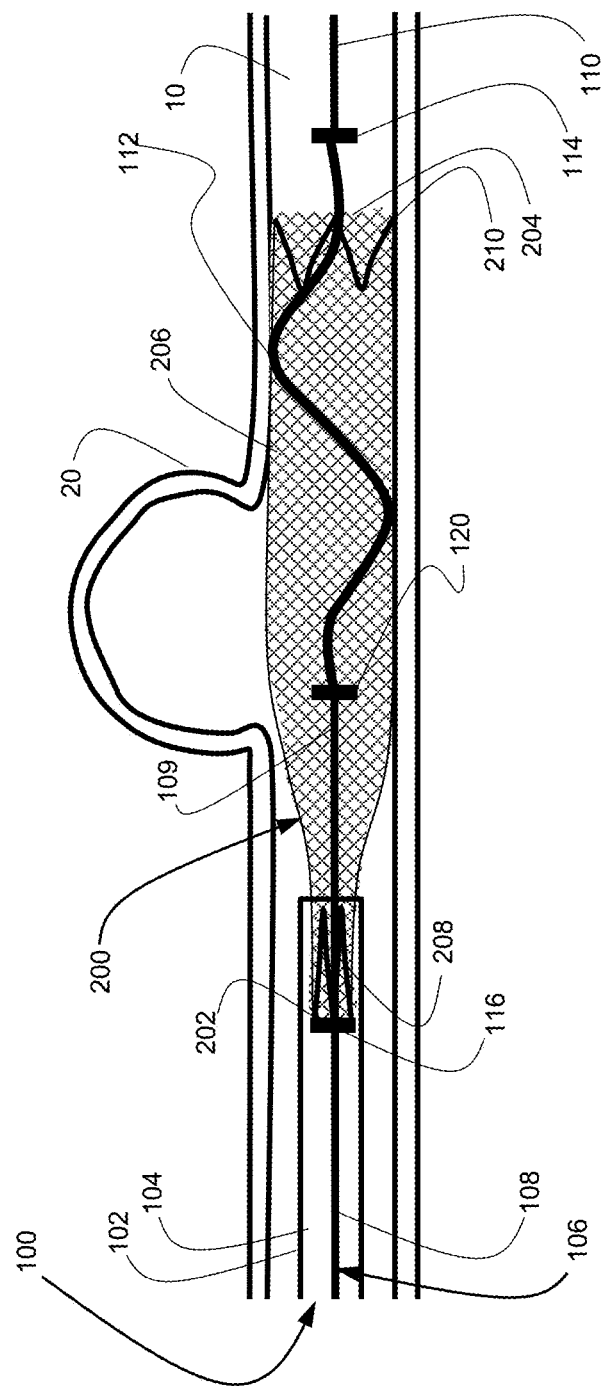

As illustrated in FIG. 2E, when the expandable element 200 is in the partially implanted configuration, the delivery wire 106 can further be moved distally to engage the proximal, pusher bump 116 with the proximal anchor 208.

Figure 2F:
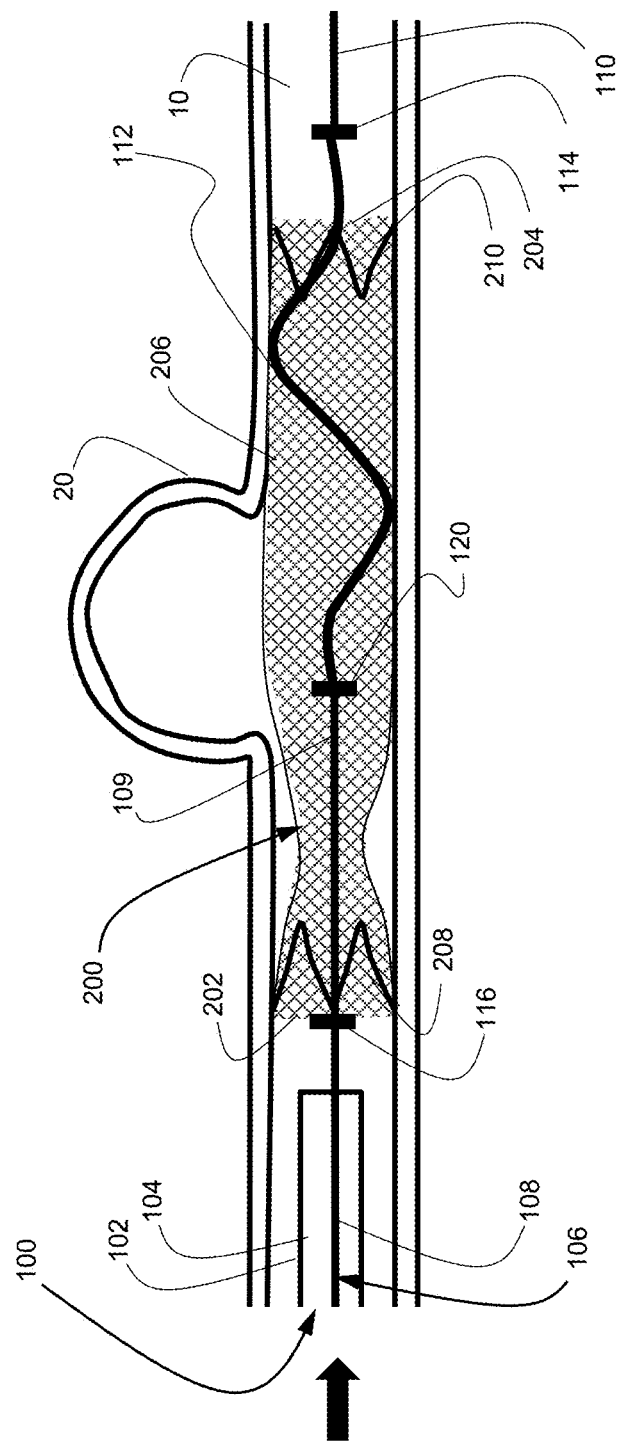

As illustrated in FIG. 2F, further distal movement of the delivery wire 106 can expel the proximal anchor 208 from the catheter 102. Once the proximal anchor 208 is expelled from the catheter 102, the proximal anchor can expand to engage the walls of the body lumen 10. Once the proximal anchor 208 is expanded, the expandable element 200 can be disengaged from the delivery wire 106. As illustrated in FIG. 2F, portions of the expandable element 200 may remain not completely conforming to the walls of the body lumen 10.

Figure 2G:
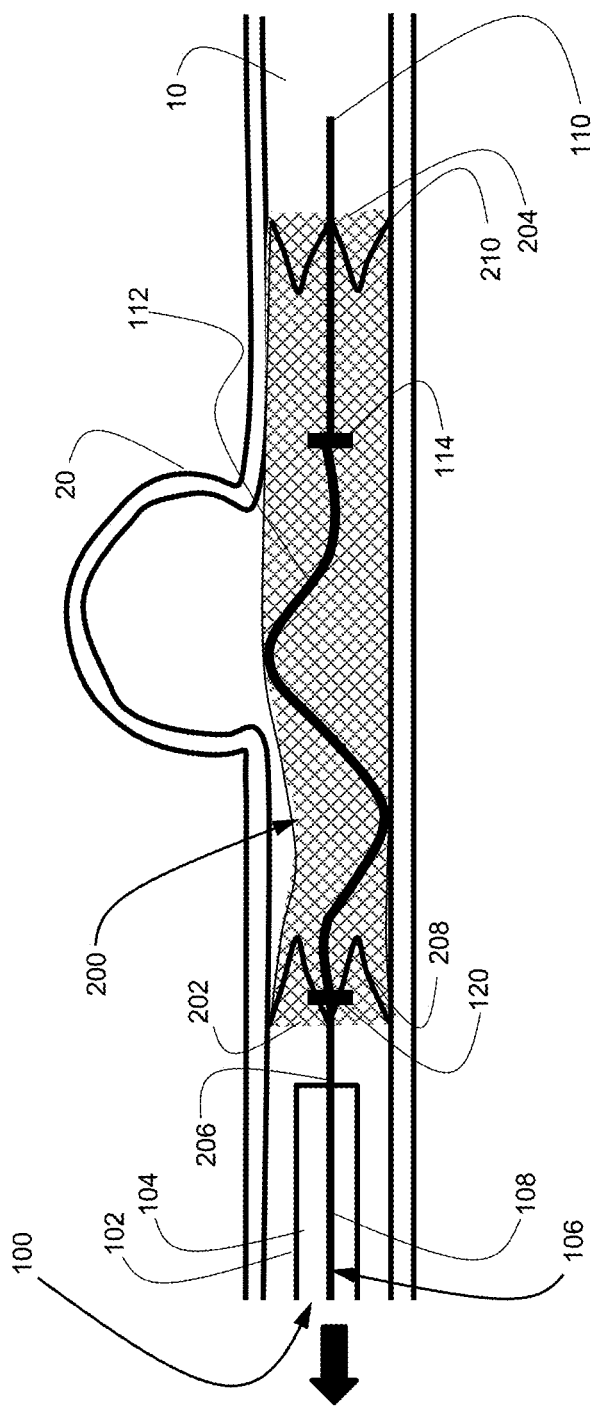

As illustrated in FIG. 2G, the delivery wire 106 can subsequently be moved proximally to slide against portions of the braid, resulting in better conformity to the walls of the body lumen 10.

Figure 2H:
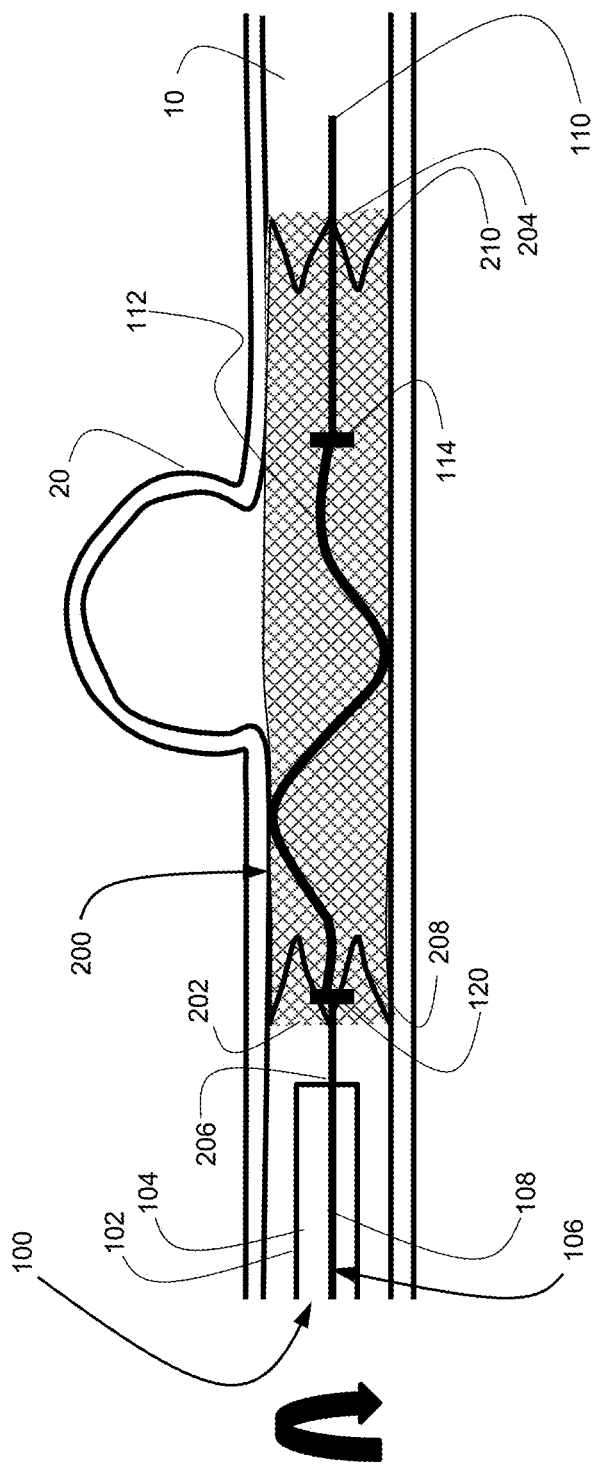

As illustrated in FIG. 2H, the delivery wire 106 can subsequently be rotated, and the shaped portion 112 can slide against portions of the braid, resulting in better conformity to the walls of the body lumen 10.

In the expanded configuration, as illustrated in FIG. 2H, the expandable element 200 can be expanded to conform to the dimensions of the patient's body lumen 10. The expanded dimension of the expandable element 200 allows the apparatus 100 to pass therethrough, to either advance to a second location or be withdrawn. The expandable element 200 can be expandable at least in part under its inherent proprieties, based at least on its original shape and the nature of the materials that make up the element, and further expanded by movement of the delivery wire 106 as described herein. Examples of the expandable element 200 can be one of pear shaped, ovoid, and elliptical when at its expanded diameter. The construction of the expandable element 200 is known to those of skill in the art. Other embodiments are contemplated for expandable elements 200 of this disclosure and can also be observed in U.S. Pat. Pub. 2016/0058524, a reference that is incorporated in its entirety herein.

Figure 3A:
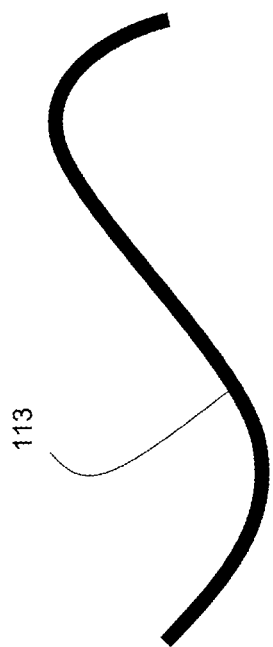
FIGS. 3A to 3C are drawings depicting shapes of a delivery wire portion according to the present invention.
Figure 3C:
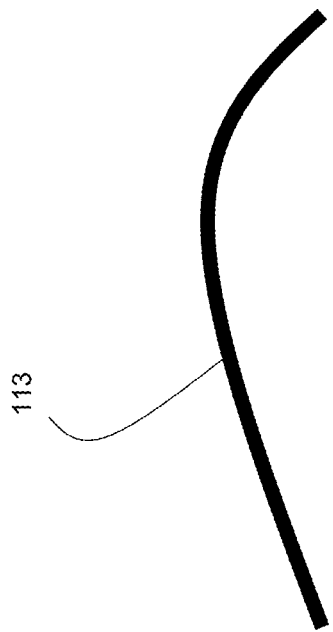
Figure 3B:
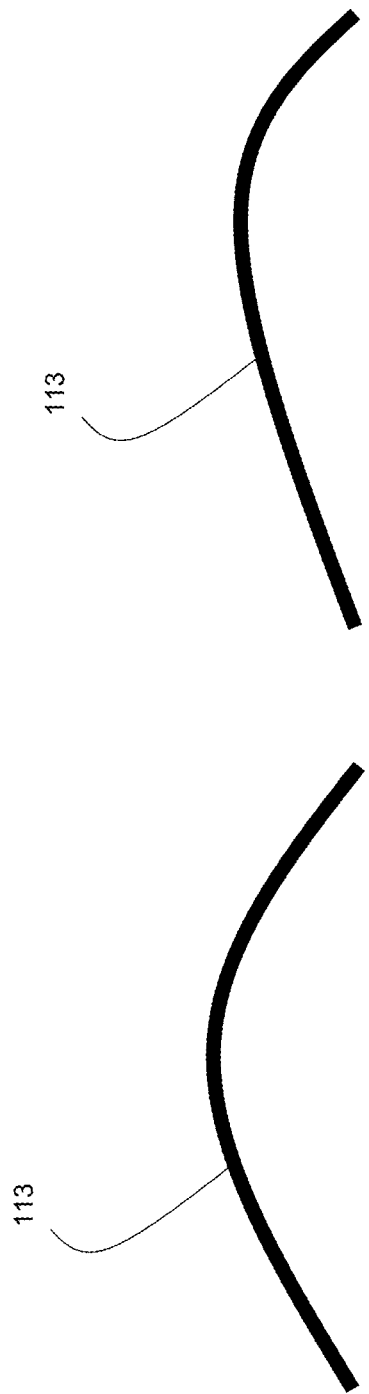

FIGS. 3A to 3C illustrate some potential shapes that a shapeable portion 112 of the delivery wire 106 can have when the expandable element is in a partially implanted configuration. Arced, curved, "S" and "C" shaped are some examples. In one example, the shapeable portion 112 presents an atraumatic section 113 to contact both the braided implant 200 and possibly the wall of the body lumen 10. This atraumatic section 113 minimizes damage to one or both of the implant 200 and lumen 10. Another example of an atraumatic section 113 is to minimize the amount of radial force applied once the shapeable portion 112 deforms from the straight to curved shape. Too much force, even applied by an atraumatic shape 113, can still damage the implant/lumen. Too little force or shape and the implant will not open to its full potential shape.

Figure 4:
FIG. 4 is an image depicting a braided implant having a segment poorly apposed to a vessel wall as known in the art.

FIG. 4 depicts a braided implant having a segment poorly apposed to a vessel wall as known in the art. It is an object of the present invention to provide devices, systems, and methods of treatment for improving conformity of an implant to a vessel wall.

Figure 5:
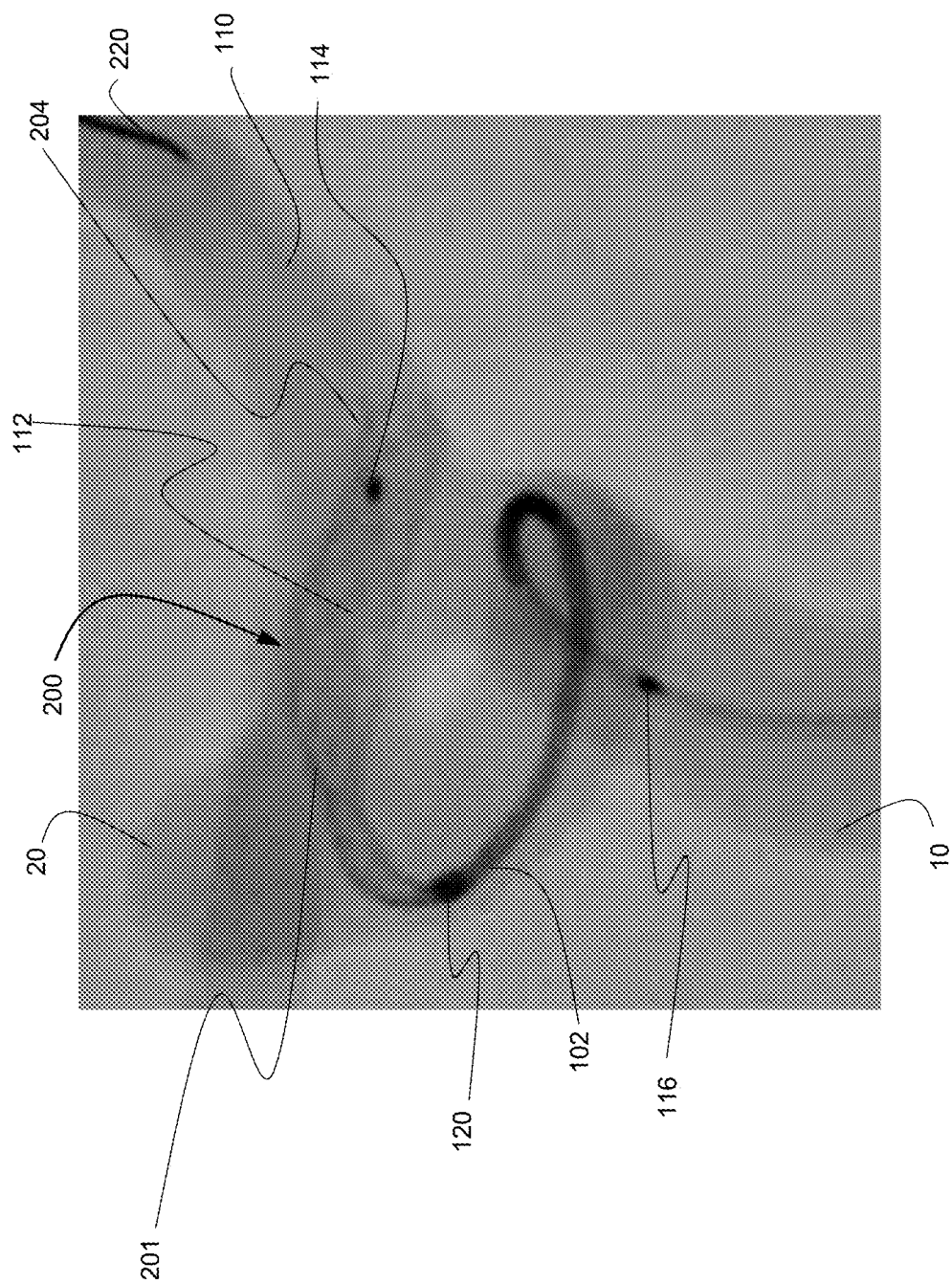
FIG. 5 is an image depicting an implantation system during implantation according to the present invention.

FIG. 5 depicts a partially implanted expandable element that is a braided implant 200 having a distal end 204 positioned outside a catheter 102 and a delivery wire 106 positioned inside the implant 200, the delivery wire 106 having a distal coil 220 positioned distal the implant 200, a distal bump 114 positioned inside the implant, a recapture bump 120 positioned inside the implant 200 proximal the distal bump 114, and proximal bump 116 positioned proximal the implant 200 inside the catheter 102. The implant 200 as depicted in FIG. 5 has a poorly apposed portion 201 that is not extended to conform to the vasculature 10.

FIGS. 6A to 6C illustrate movement of the delivery wire 106 within the system illustrated in FIG. 5 to provide an outward radial force from within the poorly apposed portion 201 and other portions of the implant 200 not fully apposed to the walls to move those portions closer to the walls of the vascular 10. Progressing from FIGS. 6A to 6B, the delivery wire 106 can be moved distally to extend against an outer curved portion of the implant 200 and/or to provide a pushing force by the proximal bump 116 against a proximal anchor (not shown) of the implant 200. Progressing from FIGS. 6B to 6C, the delivery wire 106 can be pulled proximally to press against an inner curved portion of the implant 200 and/or to retract at least a portion of the implant 200 into the catheter 102.

In the example illustrated in FIGS. 6A to 6C, the shaped portion 112 of the delivery wire 106 can be flexible to curve to the shape of a curved vasculature 10 and need not reshape as a result of being made from a memory shape material. The shapeable portion 112 can solely curve to conform to the shape of a curved bodily lumen such that distal and proximal movements of the expandable element 200, delivery wire 106, and catheter 102 can cause the delivery wire to move to provide a radial force from within the braided portion 206. In this example, the non-preshaped shapeable portion 112 can curve based on bringing the deliver wire 106 through the inside of the curve and the outside of a curve of a vasculature where the braided portion 206 is to be implanted.

Figure 7:
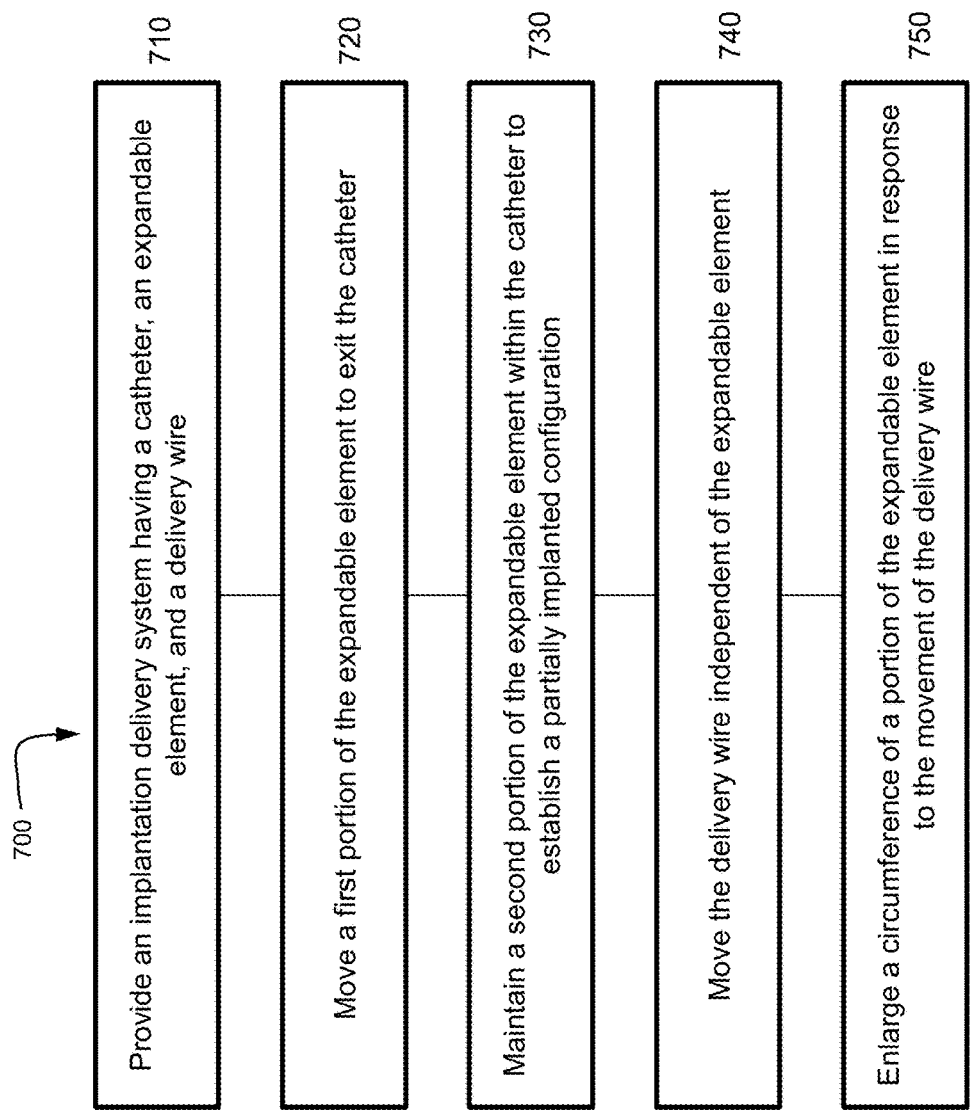
FIG. 7 is a flow diagram outlining example method steps for use of an apparatus or system for deploying an implant according to the present invention.

FIG. 7 is a flow diagram outlining example method steps for use of an apparatus or system for deploying an implant. The method steps can be implemented by an of the example means described herein or by any means that would be known to one of ordinary skill in the art.

Referring to method 700 illustrated in FIG. 7, in step 710 an implantation delivery system having a catheter, an expandable element, and a delivery wire can be provided. The implantation delivery system can be any of the delivery systems described herein having any combination of the features described here, as well as any features that would be known to one skilled in the art. In step 720 a first portion of the expandable element can be moved to exit the catheter. In step 730 a second portion of the expandable element can be maintained within the catheter to establish a partially implanted configuration. In step 740 the delivery wire can be moved independent of the expandable element in the partially implanted configuration. In step 750 a circumference of the expandable element can be enlarged in response to the movement of the delivery wire in step 740.

The descriptions contained herein are examples of embodiments of the invention and are not intended in any way to limit the scope of the invention. As described herein, the invention contemplates many variations and modifications of the implantation system and methods of use thereof, including various shapes of the shapeable portion of the delivery wire, various materials, various treatments, and various stent geometries. These modifications would be apparent to those having ordinary skill in the art to which this invention relates and are intended to be within the scope of the claims which follow.

The invention claimed is:

1. A method for implanting an expandable element comprising:
providing an implantation system comprising a catheter, the expandable element, and a delivery wire;
positioning the expandable element and at least a portion of the delivery wire within a lumen of the catheter;
moving the expandable element distally through the lumen of the catheter by pushing the delivery wire distally so that a distal bump extending from the delivery wire is pushed against a distal anchor affixed to a distal end of the expandable element;
moving a first portion of the expandable element to exit a distal end of the catheter by pushing the delivery wire distally so that the distal bump is pushed against the distal anchor, the distal anchor is expelled, and the expelled distal anchor is expanded, the first portion comprising the distal end and the distal anchor of the expandable element;
maintaining a second portion of the expandable element within the catheter to establish a partially implanted configuration of the expandable element, the second portion comprising a proximal end of the expandable element and a proximal anchor affixed to the proximal end of the expandable element;
moving the delivery wire independent of the expandable element while the expandable element is in the partially implanted configuration and while maintaining the proximal anchor within the lumen of the catheter;
enlarging a circumference of the expandable element in response to the moving the delivery wire by providing a radial force from the delivery wire against the first portion of the expandable element from within a lumen of the expandable element while the expandable element is in the partially implanted configuration;
expelling the second portion of the expandable element from the distal end of the catheter by pushing the delivery wire distally so that a proximal bump is pushed against the proximal anchor and the proximal anchor is expelled from the catheter, the proximal bump extending from the delivery wire and positioned in a proximal direction in relation to the distal bump; and
expanding the expelled proximal anchor.

2. A method comprising:
positioning an expandable element and at least a portion of a delivery wire within a lumen of a catheter;
moving the expandable element distally through the lumen of the catheter by pushing the delivery wire distally so that a distal bump extending from the delivery wire is pushed against a distal anchor affixed to a distal end of the expandable element;
moving a first portion of the expandable element to exit a distal end of the catheter by pushing the delivery wire distally so that the distal bump is pushed against the distal anchor, the distal anchor is expelled, and the expelled distal anchor is expanded, the first portion comprising the distal end and the distal anchor of the expandable element;
maintaining a second portion of the expandable element within the catheter to establish a partially implanted configuration of the expandable element, the second portion comprising a proximal end of the expandable element and a proximal anchor affixed to the proximal end of the expandable element;
shaping a portion of the delivery wire from a substantially straight configuration to a curved configuration upon a distal movement of the portion from within the lumen of the catheter to a position outside the lumen of the catheter while the expandable element is in the partially implanted configuration;
expelling the second portion of the expandable element from the distal end of the catheter by pushing the delivery wire distally so that a proximal bump is pushed against the proximal anchor and the proximal anchor is expelled from the catheter, the proximal bump extending from the delivery wire and positioned in a proximal direction in relation to the distal bump; and
expanding the expelled proximal anchor.

3. The method of claim 2 further comprising the step of sliding the shaped portion of the delivery wire against the expandable element from within a lumen of the expandable element.

4. The method of claim 2 further comprising the step of extending a portion of the expandable element to a wall of a vessel by moving the shaped portion against the expandable element.

* * * * *

UNITED STATES PATENT AND TRADEMARK OFFICE
CERTIFICATE OF CORRECTION

PATENT NO. : 10,893,963 B2
APPLICATION NO. : 16/152035
DATED : January 19, 2021
INVENTOR(S) : Robert Slazas et al.

It is certified that error appears in the above-identified patent and that said Letters Patent is hereby corrected as shown below:

On the Title Page

Related U.S. Application Data should read:
(62) Division of application No. 16/056,065, filed on Aug. 6, 2018, now Pat. No. 10,278,848.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*